(12) United States Patent
Nishimura

(10) Patent No.: US 9,011,339 B2
(45) Date of Patent: Apr. 21, 2015

(54) ULTRASONOGRAPHIC DEVICE

(75) Inventor: Yuushi Nishimura, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 823 days.

(21) Appl. No.: 13/059,584

(22) PCT Filed: Aug. 12, 2009

(86) PCT No.: PCT/JP2009/003873
§ 371 (c)(1),
(2), (4) Date: Feb. 17, 2011

(87) PCT Pub. No.: WO2010/021107
PCT Pub. Date: Feb. 25, 2010

(65) Prior Publication Data
US 2011/0144501 A1   Jun. 16, 2011

(30) Foreign Application Priority Data
Aug. 19, 2008 (JP) ................................ 2008-210667

(51) Int. Cl.
*A61B 8/00* (2006.01)
*G06T 7/00* (2006.01)
(Continued)

(52) U.S. Cl.
CPC ........................................ *A61B 8/13* (2013.01)

(58) Field of Classification Search
USPC .......................... 600/437, 407, 443, 440, 587
See application file for complete search history.

(56) References Cited

U.S. PATENT DOCUMENTS 5,680,865 A * 10/1997 Tanaka ........................... 600/441
5,833,634 A * 11/1998 Laird et al. .................... 600/587
6,542,626 B1 * 4/2003 Brouwer et al. ............... 382/128
(Continued)

FOREIGN PATENT DOCUMENTS

IN   2008-073144 A   4/2008
JP   2001-187057 A   7/2001
(Continued)

OTHER PUBLICATIONS

International Search Report for corresponding International Application No. PCT/JP2009/003873 mailed Sep. 8, 2009.
(Continued)

*Primary Examiner* — Long V Le
*Assistant Examiner* — Lawrence Laryea
(74) *Attorney, Agent, or Firm* — Lucas & Mercanti, LLP

(57) ABSTRACT

When a tomographic image is displayed, the operator of an ultrasonic diagnostic apparatus is allowed to know the timing to optimize the image quality and decide by him- or herself whether optimization needs to be done now or not.
The ultrasonic diagnostic apparatus includes: an ultrasonic probe for sending out an ultrasonic wave toward a vital tissue and receiving a reflected wave of the ultrasonic wave reflected from the tissue; an image constructing section for constructing an image frame representing a tomographic image of the tissue by calculating the magnitudes of displacements at multiple measuring sites on the tissue based on the reflected wave; a display section for displaying the image frame thereon; and a processing section for analyzing an image feature quantity of the image frame and comparing the image feature quantity to a predetermined reference feature quantity. Based on a result of the comparison, the apparatus gives a notification that it is time to decide whether its operator wants the image quality of the image frame to be optimized now or not.

10 Claims, 4 Drawing Sheets

(51) Int. Cl.
*G06K 9/46* (2006.01)
*A61B 8/13* (2006.01)

(56) References Cited

U.S. PATENT DOCUMENTS

| | | |
|---|---|---|
| 2006/0173308 A1 | 8/2006 | Sasaki |
| 2006/0241455 A1* | 10/2006 | Shvarts .................. 600/447 |
| 2007/0081711 A1 | 4/2007 | Kim et al. |
| 2007/0239005 A1 | 10/2007 | Ogasawara |
| 2009/0080040 A1* | 3/2009 | Lieberman ................ 358/504 |
| 2009/0131795 A1 | 5/2009 | Sasaki |
| 2010/0094133 A1* | 4/2010 | Yoshiara et al. ............ 600/453 |

FOREIGN PATENT DOCUMENTS

| | | |
|---|---|---|
| JP | 2004-152043 A | 5/2004 |
| JP | 2007-098142 A | 4/2007 |
| JP | 2007-195892 A | 8/2007 |
| WO | 2004/107981 A1 | 12/2004 |

OTHER PUBLICATIONS

Form PCT/ISA/237 for International Application No. PCT/JP2009/003873 dated Sep. 8, 2009 and partial English translation.

* cited by examiner

ULTRASONOGRAPHIC DEVICE

TECHNICAL FIELD

The present invention relates to a technology for displaying an image on an ultrasonic diagnostic apparatus and more particularly relates to a control technique for optimizing display of a tomographic image on an ultrasonic diagnostic apparatus.

BACKGROUND ART

An ultrasonic diagnostic apparatus is used to display a tomographic image representing an internal tissue of a subject's body. The tomographic image is generated based on an ultrasonic wave that has been sent out from an ultrasonic probe and then reflected from the internal tissue.

In this case, the tomographic image displayed will look incessantly different every time either the ultrasonic probe or the subject moves. For that reason, they say that some kind of processing for adjusting the image appearance by either increasing or decreasing the luminance of the tomographic image (which is so-called "optimization processing") should be carried out.

Some methods for carrying out such optimization on an ultrasonic diagnostic apparatus by determining the best timing are proposed in Patent Documents Nos. 1 and 2, for example.

According to Patent Document No. 1, a variation in the pixel intensity histogram of a series of image frames is monitored. And if the feature quantity of that histogram has been stabilized for a certain period but if a significant variation has been sensed in the feature quantity of the pixel intensity histogram of the latest image frame, the computer decides that the ultrasonic probe has moved and gets the image optimized automatically.

On the other hand, according to Patent Document No. 2, ultrasonic images are sampled periodically and each of those ultrasonic image sampled is divided into a number of blocks. And if a difference in feature quantity between one block of the previous sampled image and its associated block of the current sampled image has exceeded a threshold value, then it is decided that some significant change has occurred and image optimization is carried out automatically.

CITATION LIST

Patent Literature

Patent Document No. 1: Japanese Patent Application Laid-Open Publication No. 2001-187057
Patent Document No. 2: Japanese Patent Application Laid-Open Publication No. 2007-98142

SUMMARY OF INVENTION

Technical Problem

According to the methods disclosed in Patent Documents Nos. 1 and 2, however, whenever any variation is sensed in the image, optimization is automatically done by the device. That is why the operator cannot know in advance exactly when optimization needs to be done but has no choice but to confirm that the optimization has already been done by sensing a significant change of the image. This means that the optimization could be done at an unwanted timing for him or her.

On top of that, even if the quality of the image that has been optimized is not up to the operator's expectations, he or she has to look at that tomographic image continuously, which is very inconvenient for him or her.

It is therefore an object of the present invention to allow the operator of an ultrasonic diagnostic apparatus to know the timing to optimize the image and also let him or her decide whether optimization needs to be done or not. Another object of the present invention is to allow the operator who has opted to optimize the image but who has sensed that the resultant optimized image is not to his or her expectations to change the current method of displaying the image.

Solution to Problem

An ultrasonic diagnostic apparatus according to the present invention includes: an ultrasonic probe for sending out an ultrasonic wave toward a vital tissue and receiving a reflected wave of the ultrasonic wave that has been reflected from the vital tissue; an image constructing section for constructing an image frame representing a tomographic image of the tissue based on the reflected wave; a display section for displaying the image frame thereon; and a processing section for analyzing an image feature quantity of the image frame and comparing the image feature quantity to a predetermined reference feature quantity. Based on a result of the comparison, the apparatus gives a notification that it is time to decide whether its operator wants the image quality of the image frame to be optimized now or not.

The processing section may adopt, as the predetermined reference feature quantity, a result of the analysis on the previous image frame displayed.

The ultrasonic diagnostic apparatus may further include an interface section for receiving an instruction from the operator. If after the apparatus gives the notification that it is time to decide whether the operator wants the image quality of the image frame to be optimized now or not, the interface section is instructed to control the image quality, the processing section may determine a parameter for setting the image quality to be a predetermined reference value based on a result of the analysis, and the image constructing section may reconstruct the image frame in accordance with the parameter.

The ultrasonic diagnostic apparatus may further include an interface section for receiving an instruction from the operator. If after the apparatus gives the notification that it is time to decide whether the operator wants the image quality of the image frame to be optimized now or not, the interface section is instructed not to control the image quality, the processing section may change the predetermined reference feature quantity.

If after the image constructing section has reconstructed the image frame in accordance with the parameter, the interface section is instructed not to control the image quality, the image constructing section may reconstruct the image frame without adopting the parameter determined.

If the interface section is instructed not to control the image quality, the processing section may replace the predetermined reference feature quantity with the image feature quantity of the image frame.

The processing section may analyze, as the image feature quantity, a luminance related feature quantity of each of multiple areas that have been defined in the image frame.

The interface section may be a piece of hardware that allows the user to instruct the apparatus to control the image quality.

The interface section may also be a piece of hardware that allows the user to instruct the apparatus not to control the image quality.

The display section may display a sign on its screen to give the notification that it is time to decide whether the operator wants the image quality of the image frame to be optimized now or not.

The ultrasonic diagnostic apparatus may further include a light-emitting device for giving the notification, based on a result of the comparison, the operator that it is time to decide whether the operator wants the image quality of the image frame to be optimized now or not.

Advantageous Effects of Invention

According to the present invention, the operator is notified that it is time to decide whether the operator wants the image quality of the image frame to be optimized now or not. That is to say, since the image quality is not changed suddenly without notice while the apparatus is used, the operator never feels unnaturalness. On top of that, by instructing the apparatus whether the image quality of the image frame needs to be optimized or not, the operator can decide by him- or herself whether the image quality should be controlled now or not.

Also, if the operator has instructed the apparatus not to control the image quality now, the reference feature quantity that was used when the operator was notified of that timing is changed. That is why the operator will be told the time to get the image quality optimized using a different reference after that.

DESCRIPTION OF EMBODIMENTS

Hereinafter, preferred embodiments of an ultrasonic diagnostic apparatus according to the present invention will be described with reference to the accompanying drawings.

Figure 1:
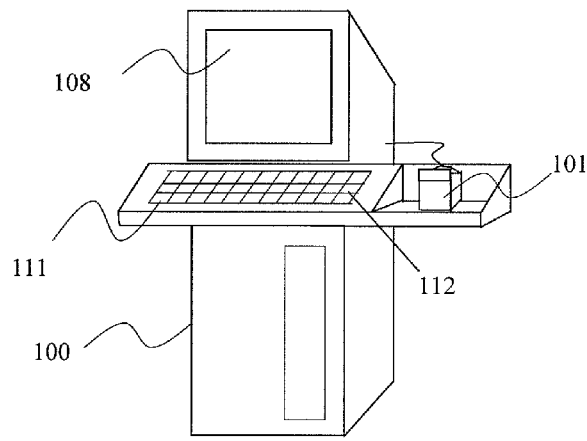
FIG. 1 illustrates the appearance of an ultrasonic diagnostic apparatus 100 as a specific preferred embodiment of the present invention.

FIG. 1 illustrates the appearance of an ultrasonic diagnostic apparatus 100 as a specific preferred embodiment of the present invention. Using an ultrasonic probe 101, the ultrasonic diagnostic apparatus 100 displays a tomographic image of an internal body tissue as an image frame on a monitor 108 in real time. At that time, the user can control the image quality and other settings using various buttons on this ultrasonic diagnostic apparatus 100 (e.g., buttons 111 and 112 on a control panel).

Figure 2:
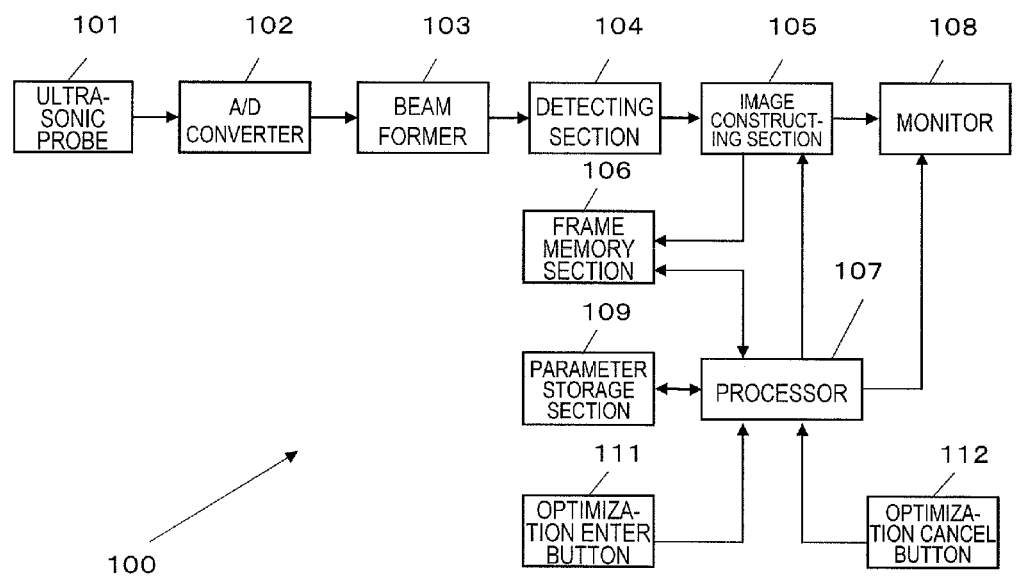
FIG. 2 is a block diagram illustrating an internal configuration for the ultrasonic diagnostic apparatus 100 of this preferred embodiment.

FIG. 2 is a block diagram illustrating an internal configuration for the ultrasonic diagnostic apparatus 100 of this preferred embodiment.

The ultrasonic diagnostic apparatus 100 includes an ultrasonic probe 101, an A/D converter 102, a beam former 103, a detecting section 104, an image constructing section 105, a frame memory section 106, a processor 107, a monitor 108, a parameter storage section 109, an optimization enter button 111 and an optimization cancel button 112.

The ultrasonic probe 101 sends out and receives an ultrasonic beam as described above.

The A/D converter 102 converts the ultrasonic reflected wave received into a digital signal. The beam former 103 performs a delayed combination on the ultrasonic wave reflected wave that has been A/D converted. And the detecting section 104 carries out an envelope detection on an ultrasonic echo signal that has been subjected to the delay combination.

The image constructing section 105 subjects the ultrasonic echo signal detected to signal processing, thereby constructing a tomographic image frame representing the tissue.

The frame memory section 106 accumulates image frames of the tomographic image. What is accumulated in the frame memory section 106 may be nothing but tomographic image frames, which may be accumulated there either for a predetermined amount of time or in a predetermined number.

The processor 107 is a so-called central processing unit (CPU) and analyzes the tomographic image frames, thereby determining whether a currently presented image needs to be processed or not. For example, the processor 106 may analyze a series of tomographic image frames to detect any variation between them. And on sensing that the luminance value has decreased to a threshold value or less, the processor 107 may determine whether the luminance of the image should be increased or not.

The monitor 108 displays the tomographic image on it.

The parameter storage section 109 stores image quality control parameters and results of image analysis.

The optimization enter button 111 conveys the operator's image optimization enter instruction to the processor 107. On the other hand, the optimization cancel button 112 conveys the operator's image optimization cancel instruction to the processor 107.

This ultrasonic diagnostic apparatus 100 operates in the following manner.

An ultrasonic beam is sent out toward the subject by the ultrasonic probe 101, reflected by his or her internal body tissue, and then received by the ultrasonic probe 101. The A/D converter 102 converts an analog signal representing the ultrasonic reflected wave received into a digital signal. And the beam former 103 performs a delay combination on that ultrasonic reflected wave.

The detecting section 104 performs an envelope detection, thereby removing transmitted wave components (i.e., carrier components) from the received signal and outputting it as an ultrasonic echo signal to the image constructing section 105.

The image constructing section 105 subjects the input ultrasonic echo signal to filtering, total gain application processing, TGC application processing, LGC application processing, frame gain application processing, scan conversion and other kinds of processing, thereby constructing an ultrasonic tomographic image frame, getting it stored in the frame memory section 106 and presenting it on the monitor 108.

The processor 107 retrieves an image frame from the frame memory section 106 and analyzes the feature quantity of that image. As used herein, the "feature quantity" may refer to the luminance value of each of multiple regions that have been defined in the image or their standard deviation, for example.

Furthermore, the processor 107 compares the result of this analysis to the result of the previous analysis that has been obtained from the parameter storage section 109, thereby determining whether or not there is any significant difference (such as a variation in luminance value, of which the magnitude exceeds a predetermined threshold value) between those two image frames. In this case, the "result of the previous analysis" refers to the result of the analysis that was performed on an image frame when the optimization enter button 111 was pressed by the operator last time.

And if there is any significant difference between them, the processor 107 decides that the time has come when the operator has to decide whether he or she wants the image quality to be controlled (or optimized) now or not (such a timing will be referred to herein as an "optimization timing") and gives a notification to him or her or that by displaying a sign on the monitor. Instead of displaying such a sign on the monitor 108, the operator may also be notified by blinking a light-emitting device such as an LED built in the optimization enter button 111 on the control panel or an LED (not shown) that is provided separately from the button.

It should be noted that the terms "control" and "optimization" herein have the same meaning. The "optimization processing" to be described later is a kind of processing for improving the image quality. That is why after the optimization processing has been done, it can be said that the image quality is higher than ever. For that reason, such a state in which the image quality has been improved to the maximum degree up to a certain point in time will be referred to herein as either an "optimized" state or a "controlled" state.

Figure 3:
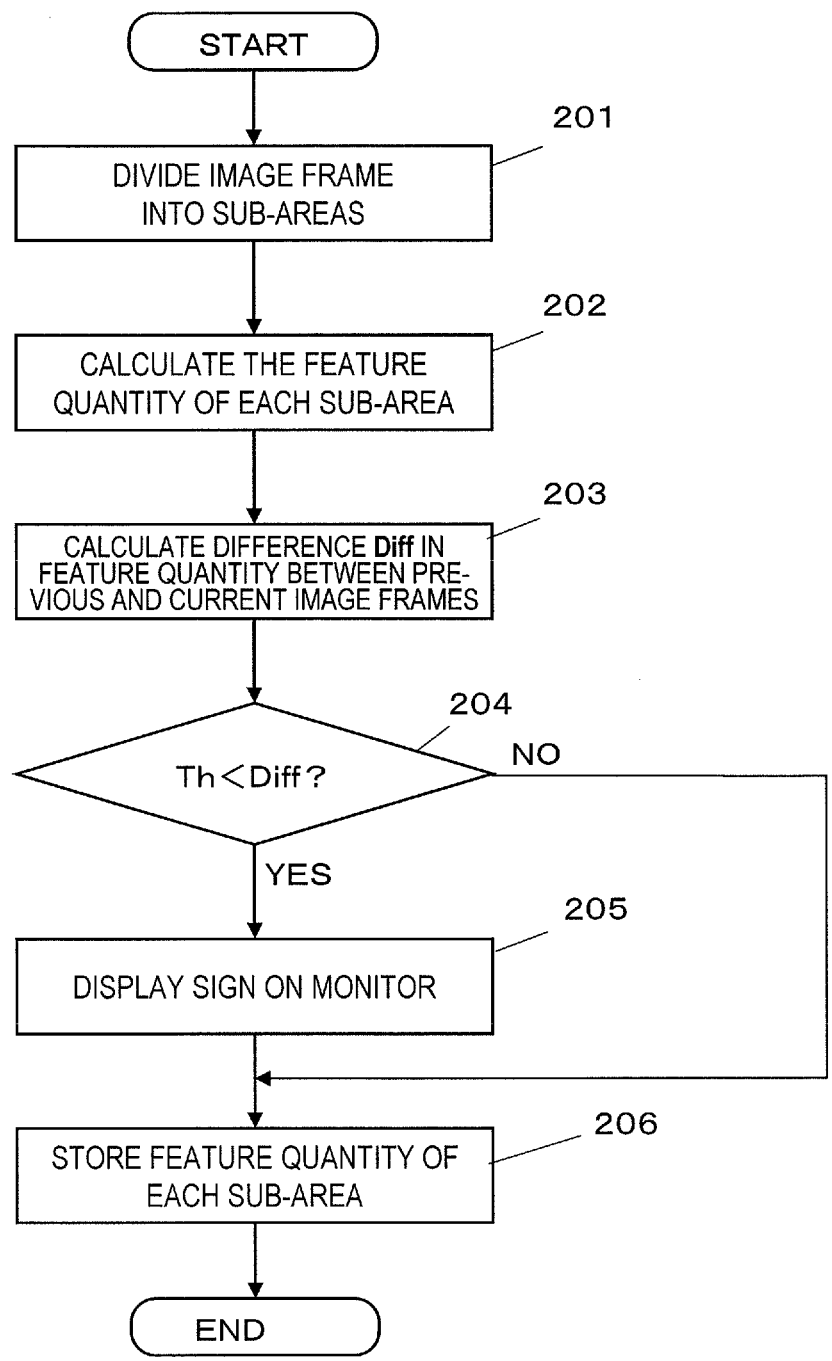
FIG. 3 is a flowchart showing the processing to get done by a processor 107 to determine whether it is the optimization timing or not.

FIG. 3 shows the sequence of the processing to get done by the processor 107 to determine whether it is the optimization timing or not.

Figure 4:
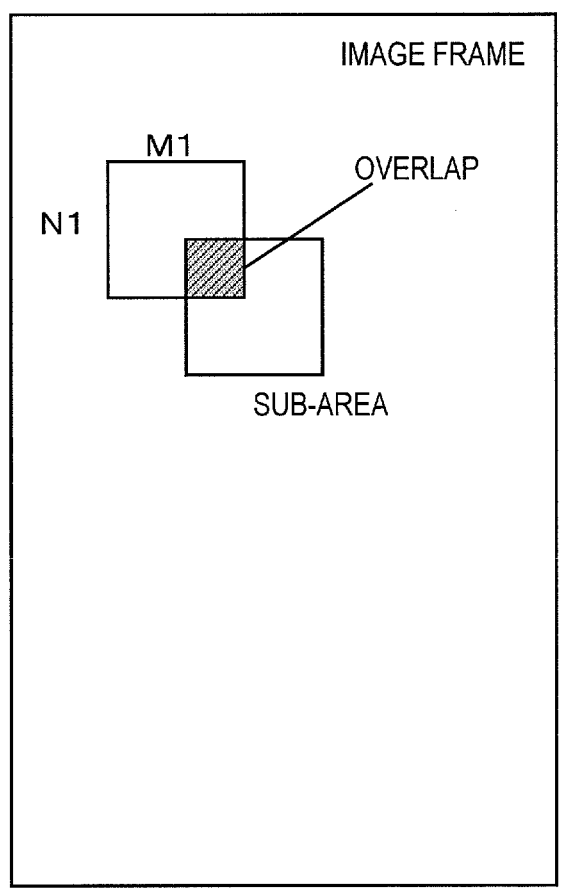
FIG. 4 illustrates two sub-areas that overlap with each other.

First of all, in Step 201, the processor 107 divides a given image frame into a number of sub-areas, each having a width M and a height N that may have been set to be arbitrary values in advance. In this preferred embodiment, those sub-areas are defined to be completely separate ones that never overlap with each other. However, this is just an example and those sub-areas could overlap with each other. FIG. 4 illustrates two sub-areas that overlap with each other. The respective sub-areas may also be defined in this manner, too.

Next, in Step 202, the processor 107 calculates the feature quantity of every sub-area. In this preferred embodiment, the standard deviation of the luminance values of all pixels in each sub-area is used as the feature quantity. As the feature quantity, not just the standard deviation but also some statistic such as an average, a median, or a coefficient of variation or the sum of power spectra of the images could be used as well.

Subsequently, in Step 203, the processor 107 retrieves the previous sub-area feature quantity from the parameter storage section 109, calculates the absolute value of the difference between the previous and current feature quantities on a sub-area basis and then calculates the sum of those differences, thereby obtaining a feature quantity difference Diff between the previous and current image frames.

Thereafter, in Step 204, the processor 107 compares a preset threshold value Th to Diff. If the processor 107 finds Diff greater than the threshold value Th, then the processor 107 decides that it is time to update the image quality. Then, the process advances to Step 205.

In Step 205, the processor 107 notifies the operator that the optimization timing has come. In this processing step, the notification may be made either by displaying a sign on the monitor 108 or by blinking the light-emitting device just as described above.

Finally, in Step 206, the processor 107 stores the feature quantity of each sub-area that has been calculated this time in the parameter storage section 109 so that the feature quantity can be used for analysis next time.

When the sign indicating that the optimization timing has come is displayed in Step 205, the operator can get the image optimized by pressing the optimization enter button 111.

Next, it will be described what processing will be performed after such a sign indicating that the optimization timing has come has been displayed.

Figure 5:
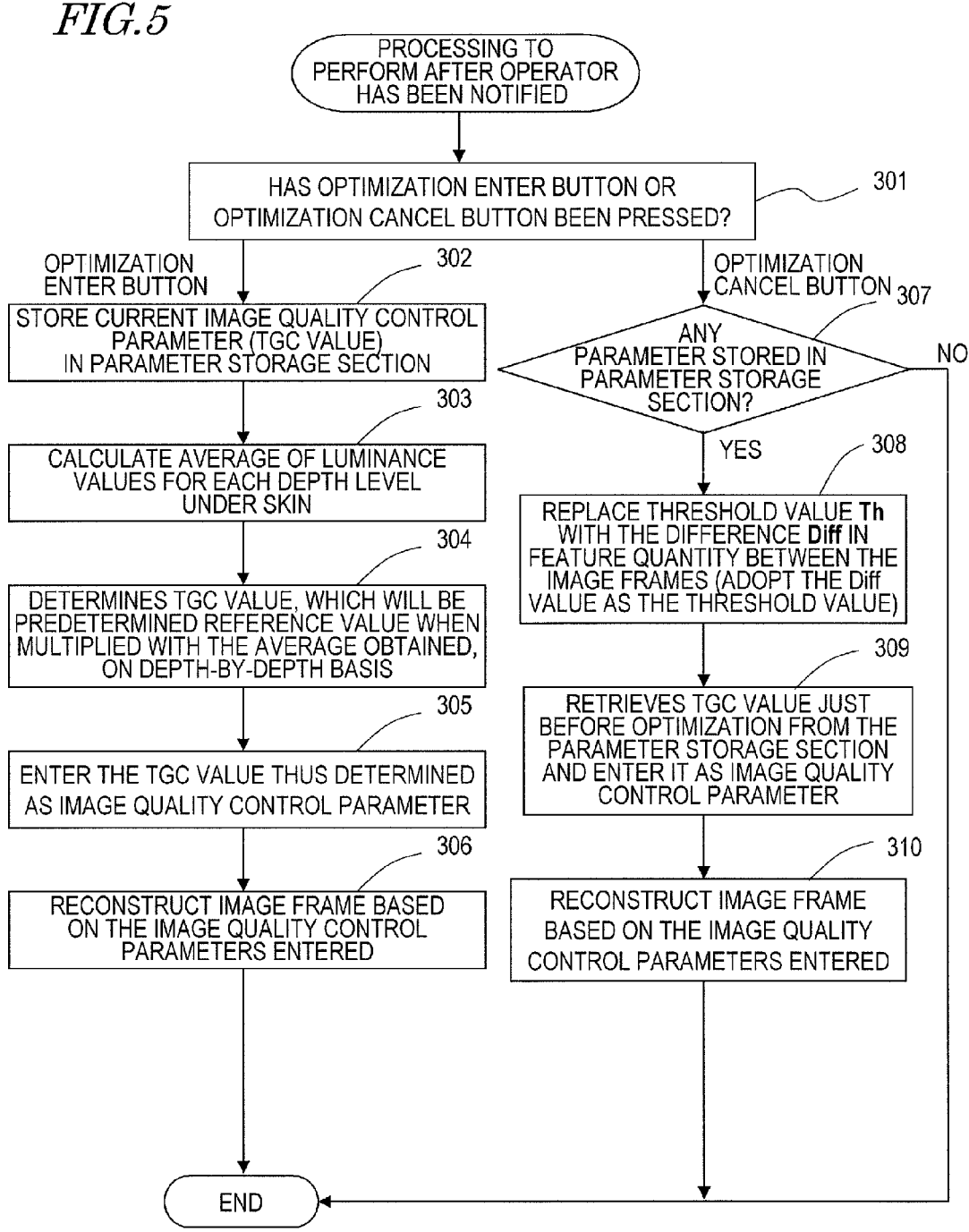
FIG. 5 is a flowchart showing the procedure of the processing to get done after the operator has been notified.

FIG. 5 is a flowchart showing the procedure of the processing to get done after the operator has been notified.

First, in Step 301, the processor 107 determines whether the operator has pressed the optimization enter button 111 or the optimization cancel button 112. If the optimization enter button 111 has been pressed, the process advances to Step 302. On the other hand, if the optimization cancel button 112 has been pressed, then the process advances to Step 307.

If the optimization enter button 111 has been pressed, the processor 107 stores in Step 302 the current image quality control parameters in the parameter storage section 109 just before the settings are changed. And the processor 107 performs a series of processing steps 303 to, thereby calculating image quality control parameters to optimize the image and entering those parameters into the image constructing section 105. Thereafter, in Step 306, the image constructing section 105 reconstructs an image frame based on the image quality control parameters entered and then outputs the reconstructed image frame to the monitor 108.

Specifically, those processing steps 303 through 306 are performed in the following manner.

First, the image quality control parameters for optimizing the image may be calculated by any of various methods. As an example, the processing of optimizing a TGC (time gain control) value will be described.

As used herein, the "TGC" means a control to be performed to reduce a variation in the lightness of an image within an image frame. Generally speaking, if an ultrasonic wave is used, its reflected wave will attenuate more steeply when reflected from a deeper region under the skin than when reflected from a shallower region under the skin. That is why an image representing that deeper region tends to darken. Thus, to overcome such a problem, the ultrasonic diagnostic apparatus 100 of this preferred embodiment classifies the depths under the skin 2 into seven levels, for example, and is ready to control the image lightness for each of those seven grades. As a result, the gain control can be done on a depth-by-depth basis so that an image frame can always be displayed with its lightness controlled according to the operator's preference, no matter whether the image frame represents a shallow region or a deep region under the skin. For instance, the image frame can always be displayed with its lightness kept constant at each and every depth. Or an image frame representing an internal body tissue that is located deep under the skin may be displayed with an increased lightness. And it is the TGC value that is used in such a depth-by-depth gain control.

The processing of optimizing the TGC value may be carried out as follows. Specifically, in Step 303, the processor 107 calculates the average of luminance values for each depth level under the skin 2 in the image frame. Next, in Step 304, the processor 107 determines a TGC value, which will be a predetermined reference value when multiplied with the average that has been calculated in the previous step, on a depth-by-depth basis again. In this preferred embodiment, the depths under the skin 2 are classified into seven levels and the image quality may be controlled adaptively according to the depth in question.

Then, in Step 305, the processor 107 enters the TGC value thus determined as an image quality control parameter into the image constructing section 105.

And in Step 306, the image constructing section 105 reconstructs an image frame based on the image quality control parameters entered and then outputs the image frame thus obtained to the monitor 108.

In some cases, even if the operator has pressed the optimization enter button 111, he or she may press the optimization cancel button 112 after the optimization has been done.

In that case, the process advances to Step 307, in which the processor 107 sees if any parameter is stored in the parameter storage section 109. As can be seen from the processing step 302, if the optimization enter button 111 has ever been pressed at least once, some parameter will be stored in the parameter storage section 109.

But if the optimization enter button 111 has never been pressed yet, no parameters will be stored in the parameter storage section 109. In that case, the processor 107 ends this processing. But if any parameter is stored in the parameter storage section 109, then the process advances to Step 308, in which the processor 107 replaces the threshold value Th with the difference Diff in feature quantity between the image frames. As a result, that Diff value will be used as the threshold value when it is determined next time whether or not it is time to make optimization. Then, the image frame on the monitor 108 does not change at all.

Next, in Step 309, the processor 107 retrieves the TGC value just before the optimization from the parameter storage section 109 and enters it as an image quality control parameter into the image constructing section 105. This means that the optimization processing that has been carried out once has been canceled. Then, in Step 310, the image constructing section 105 reconstructs an image frame based on the image quality control parameter entered and then outputs the reconstructed image frame to the monitor 108.

It should be noted that this processing step of entering the image quality control parameter just before the optimization into the image constructing section 105 is only an example. Anyway, as the user is not satisfied with the currently presented image, the way of displaying that image is preferably changed again. For that reason, instead of adopting the image quality control parameter just before the optimization, the types of image processing may be changed again and again until the user gets fully satisfied.

If the operator has pressed the optimization cancel button 112, it means that he or she does not want to get the image quality optimized at that point in time. In other words, it indicates that the optimization standard presented at that point in time by the ultrasonic diagnostic apparatus 100 does not agree with the operator's. Thus, by changing the threshold value as described above, the threshold value can be even closer to the operator's optimization standard.

In the foregoing description of preferred embodiments, the frame storage section 106 is supposed to accumulate image frames of a tomographic image. However, image feature quantities, which are results of analysis on image frames, may be accumulated instead of the image frames themselves. As a result, the space left in the frame memory section 106 can saved.

Also, in the preferred embodiment described above, the user interface means that allows the operator to indicate whether or not he or she wants to get optimization done now is supposed to be the optimization enter button 111 and the optimization cancel button 112, which are pieces of hardware. However, this is just an example. Alternatively, the monitor 108 may be implemented as a touchscreen panel that displays the buttons 111 and 112 thereon. In that case, portions of the touchscreen panel corresponding to the respective display locations of the optimization enter and cancel buttons 111 and 112 are used as the user interface means. Still alternatively, two dialog boxes that perform the same function as the buttons 111 and 112 may be displayed on the monitor 108 so as to be selectively entered with a mouse or a keyboard. In that case, the user interface means is the mouse or the keyboard.

The procedures of processing that have been described with reference to the flowchart shown in FIGS. 3 and 5 may be carried out as a computer program to be executed by the processor 107. Such a computer program may be circulated on the market by being either stored on a storage medium such as a CD-ROM or downloaded over telecommunications lines such as the Internet. The processor 107 of the ultrasonic diagnostic apparatus 100 may be implemented as a general-purpose processor (i.e., a semiconductor integrated circuit) that can execute the computer program. Alternatively, the processor 107 may also be a dedicated processor in which such a computer program has been installed.

INDUSTRIAL APPLICABILITY

The ultrasonic diagnostic apparatus of the present invention can notify the user that it may be high time to optimize the image quality of a subject's tomographic image and prompts the user to decide by him- or herself whether or not the quality of the image presented should be optimized now. Consequently, according to the present invention, the user can check out the image after having its quality controlled according to his or her preference.

REFERENCE SIGNS LIST 100 ultrasonic diagnostic apparatus
101 ultrasonic probe
102 A/D converter
103 beam former
104 detecting section
105 image constructing section
106 frame memory section
107 processor
108 monitor
109 parameter storage section
111 optimization enter button
112 optimization cancel button

The invention claimed is:
1. An ultrasonic diagnostic apparatus comprising:
an ultrasonic probe configured to send out an ultrasonic wave toward a vital tissue and to receive a reflected wave of the ultrasonic wave that has been reflected from the vital tissue;
an image signal processor configured to construct an image frame representing a tomographic image of the tissue based on the reflected wave;
a display configured to display the image frame thereon;
a processor configured to analyze an image feature quantity of the image frame and to compare the image feature quantity to a predetermined reference feature quantity; and
a user interface configured to receive an instruction from an operator;
wherein based on a result of the comparison, the processor is configured to give a notification of a time to decide whether the operator wants the image quality of the image frame to be optimized now or not,
wherein when the processor gives the notification of the time to decide whether the operator wants the image quality of the image frame to be optimized now or not, and the user interface receives an instruction not to optimize the image quality, in response to the instruction not to optimize the image quality, the processor replaces the predetermined reference feature quantity with the image feature quantity of the image frame, thereby updating the predetermined reference feature quantity, wherein when the processor dives the notification of the time to decide whether the operator wants the image of the image frame to be optimized now or not, and the user interface receives an instruction to control the image now, in response to the instruction to optimize the image quality now, the processor calculates image quality optimize parameters for optimizing the image.

2. The ultrasonic diagnostic apparatus of claim 1, wherein the processor adopts, as the predetermined reference feature quantity, a result of the analysis on a previous image frame displayed.

3. The ultrasonic diagnostic apparatus of claim 1, wherein when the processor gives the notification of the time to decide whether the operator wants the image quality of the image frame to be optimized now or not, and the user interface receives an instruction to control the image quality, in response to the instruction to control the image quality, the processor determines a parameter for setting the image quality to be a predetermined reference value based on a result of the analysis, and the image signal processor reconstructs the image frame in accordance with the parameter.

4. The ultrasonic diagnostic apparatus of claim 3, wherein when the image signal processor has reconstructed the image frame in accordance with the parameter, and the user interface is instructed not to optimize the image quality, the image signal processor reconstructs the image frame without adopting the parameter determined.

5. The ultrasonic diagnostic apparatus of claim 1, wherein the processor analyzes, as the image feature quantity, a luminance related feature quantity of each of multiple areas that have been defined in the image frame.

6. The ultrasonic diagnostic apparatus of claim 1, wherein the user interface is a piece of hardware that allows the operator to instruct the apparatus to optimize the image quality.

7. The ultrasonic diagnostic apparatus of claim 1, wherein the user interface is a piece of hardware that allows the operator to instruct the apparatus not to optimize the image quality.

8. The ultrasonic diagnostic apparatus of claim 1, wherein the display displays a sign on a screen to give the notification of the time to decide whether the operator wants the image quality of the image frame to be optimized now or not.

9. The ultrasonic diagnostic apparatus of claim 1, further comprising a light-emitting device for giving the notification, based on a result of the comparison, of the time to decide whether the operator wants the image quality of the image frame to be optimized now or not.

10. In an ultrasonic diagnostic apparatus, the apparatus comprising an ultrasonic probe configured to send out an ultrasonic wave toward a vital tissue and to receive a reflected wave of the ultrasonic wave that has been reflected from the vital tissue; an image signal processor configured to construct an image frame representing a tomographic image of the tissue based on the reflected wave; a display configured to display the image frame thereon; a processor, and a user interface configured to receive an instruction from an operator a computer program, stored on a non-transitory computer-readable medium, wherein the computer program makes the processor perform the steps of:

analyzing an image feature quantity of the image frame;

comparing the image feature quantity to a predetermined reference feature quantity; giving a notification, based on a result of the comparison, of a time to decide whether the operator wants the image quality of the image frame to be optimized now or not;

wherein when the processor gives the notification of the time to decide whether the operator wants the image quality of the image frame to be optimized now or not, and the user interface receives an instruction not to optimize the image quality, in response to the instruction not to optimize the image quality, the processor replaces the predetermined reference feature quantity with the image feature quantity of the image frame, thereby updating the predetermined reference feature quantity, wherein when the processor gives the notification of the time to decide whether the operator wants the image quality of the image frame to be optimized now or not, and the user interface receives an instruction to optimize the image now, in response to the instruction to optimize the image quality now, the processor calculates image quality control parameters for optimizing the image.

* * * * *